United States Patent [19]

Quagliato

[11] Patent Number: 5,171,857
[45] Date of Patent: Dec. 15, 1992

[54] ANTIHYPERTENSIVE BENZOPYRAN DERIVATIVES

[75] Inventor: Dominick A. Quagliato, Edison, N.J.

[73] Assignee: American Home Products Corporation, New York, N.Y.

[21] Appl. No.: 773,186

[22] Filed: Oct. 8, 1991

Related U.S. Application Data

[63] Continuation-in-part of Ser. No. 753,256, Aug. 30, 1991, abandoned, which is a continuation of Ser. No. 502,084, Mar. 29, 1990, abandoned.

[51] Int. Cl.$^5$ ............................................. C07D 471/04
[52] U.S. Cl. ..................................... 546/113; 548/484
[58] Field of Search ........................ 548/484; 546/113

[56] References Cited

U.S. PATENT DOCUMENTS 4,616,021 10/1986 Ashwood et al. .................. 548/454

FOREIGN PATENT DOCUMENTS 0158923 7/1990 European Pat. Off. .

Primary Examiner—David B. Springer
Attorney, Agent, or Firm—Walter Patton

[57] ABSTRACT

Disclosed herein are novel benzopyrans represented by formula (I)

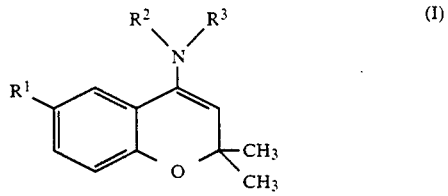

wherein $R^1$ is trifluoromethoxy or $\beta, \beta, \beta$-trifluoroethoxy; $R^2$ and $R^3$ are independently selected from the group consisting of hydrogen, lower alkyl containing 1 to 5 carbon atoms, cyclo lower alkyl containing 5 to 8 carbon atoms,

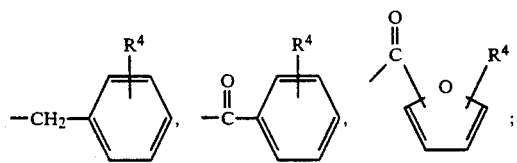

or $R^2$ and $R^3$ are joined to form $(-CH_2-)_n$ wherein n is 4 to 7; or $R^2$ and $R^3$ are joined together to form $(-CH_2-)_m CO-$ wherein m is 3 to 6; or $R^2$ and $R^3$ are joined together to form

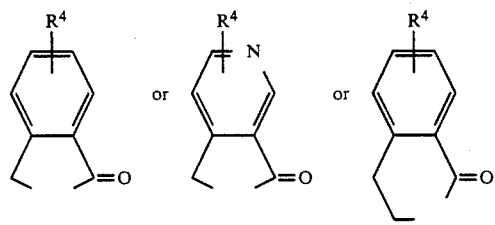

wherein $R^4$ is selected from the group consisting of hydrogen, alkoxy containing 1 to 5 carbon atoms, amino or mono- or disubstituted alkyl amino wherein said alkyl groups contain 1 to 5 carbon atoms and the pharmaceutically acceptable salts and solvates thereof, to a process for preparing them, to pharmaceutical compositions containing them, and to their use in the treatment of hypertension, asthma, irritable bladder syndrome, and irritable bowel syndrome.

1 Claim, No Drawings

ANTIHYPERTENSIVE BENZOPYRAN DERIVATIVES

This is a continuation-in-part application of copending application U.S. Ser. No. 07/753,256, filed Aug. 30, 1991, abandoned which, in turn, is a continuation application of copending application U.S. Ser. No. 07/502,084, filed Mar. 29, 1990, now abandoned.

BACKGROUND OF THE INVENTION

The present invention relates to novel benzopyrans having pharmacological activity, to a process for preparing them, to pharmaceutical compositions containing them, and to their use in the treatment of hypertension.

European Patent Publication No. 158,923 discloses classes of chromans that are described as having blood pressure lowering activity.

The present invention discloses compounds represented by formula (I)

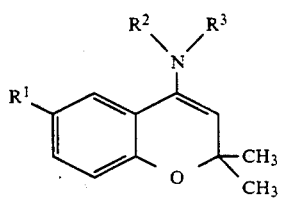

wherein $R^1$ is trifluoromethoxy or $\beta, \beta, \beta$-trifluoroethoxy; $R^2$ and $R^3$ are independently selected from the group consisting of hydrogen, lower alkyl containing 1 to 5 carbon atoms, cyclo lower alkyl containing 5 to 8 carbon atoms,

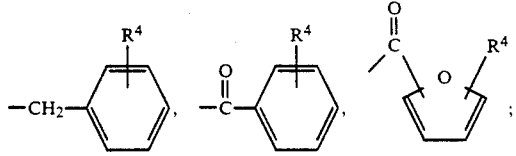

or $R^2$ and $R^3$ are joined to form $(-CH_2-)_n$ wherein n is 4 to 7; or $R^2$ and $R^3$ are joined together to form $(-CH_2-)_m CO-$ wherein m is 3 to 6; or $R^2$ and $R^3$ are joined together to form

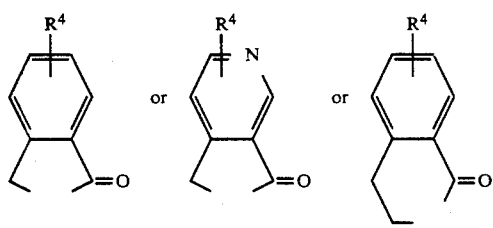

wherein $R^4$ is selected from the group consisting of hydrogen, alkoxy containing 1 to 5 carbon atoms, amino or mono- or disubstituted alkyl amino wherein said alkyl groups contain 1 to 5 carbon atoms and the pharmaceutically acceptable salts and solvates thereof.

Preferred aspects of the present invention are compounds of formula (I) wherein $R^1$ is trifluoromethoxy and $R^2$ and $R^3$ are joined to form

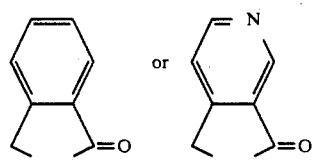

and the pharmaceutically acceptable salts and solvates thereof.

The preferred compounds of the present invention are designated
2-[2,2-dimethyl-6-(trifluoromethoxy)-2H-1-benzopyran-4-yl]-2,3-dihydro-1H-isoindol-1-one,
2-[2,2-dimethyl-6-(trifluoromethoxy)-2H-1-benzopyran-4-yl]-1,2-dihydro-3H-pyrrolo[3,4-c]pyridin-3-one,
and the pharmaceutically acceptable salts thereof.

The present invention provides a process for the production of compounds of formula (I) which comprises the reaction of a compound of formula (II)

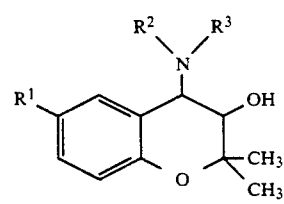

wherein $R^1$, $R^2$, and $R^3$ are as defined above with NaH, $CS_2$ and MeI to form the substituted intermediate xanthate compound of formula (III)

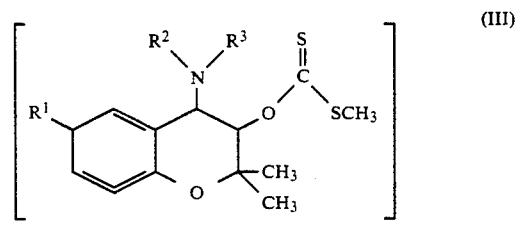

wherein $R^1$, $R^2$, and $R^3$ are as defined above and heating said xanthate compound of formula (III) to produce the compound of formula (I).

Alternatively, compounds of formula (II) wherein $R^1$, $R^2$, and $R^3$ are as defined above are condensed with methanesulfonyl chloride in the presence of triethylamine to afford the intermediate methanesulfonate of the formula (IIIa)

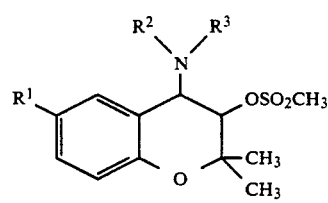

wherein $R^1$, $R^2$, and $R^3$ are as defined above. Said methanesulfonate (IIIa) is treated sequentially with sodium iodide (at room temperature) and 1,8-diazabicyclo[5.4.-0]undec-7-ene (DBU) at slightly elevated temperature to produce the compound of formula (I).

Some of the required compounds of formula (II) can be prepared by the reaction of a compound of formula (IV)

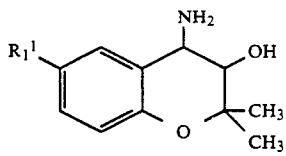 (IV)

where $R_1{}^1$ is $R^1$ as defined hereinbefore or a group or atom convertible thereto, with a compound of formula (V)

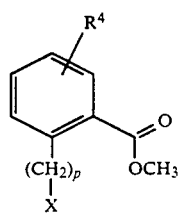 (V)

wherein X is chlorine, bromine, or iodine; $R^4$ is as defined above; and p is 1 or 2 to produce the compound of formula (VIIa).

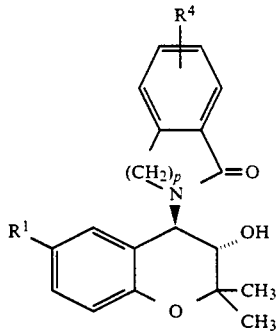 (VIIa)

wherein $R^1$, $R^4$ and p are as defined above.

Some of the required compounds of formula (II) can be prepared by the reaction of a compound of formula (IV)

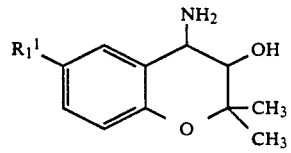 (IV)

wherein $R_1{}^1$ is $R^1$ as defined hereinbefore or a group or atom convertible thereto, with a compound of formula (VIa) or (VIb)

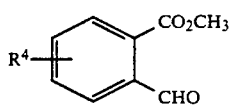 (VIa)

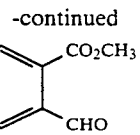 (VIb)

wherein $R^4$ is as defined above to produce the compound of formula (VIIa), wherein p is 1 or VIIb

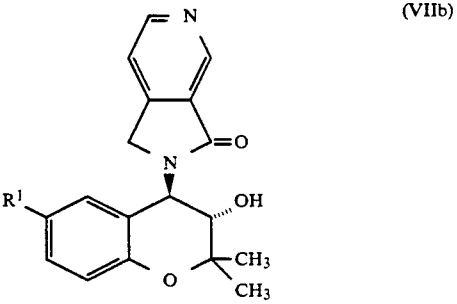 (VIIb)

wherein $R^1$ is as defined above.

The present invention provides a process for the reaction of the compound (VIIa) with NaH, $CS_2$ and MeI to form the substituted intermediate xanthate compound of formula (VIII)

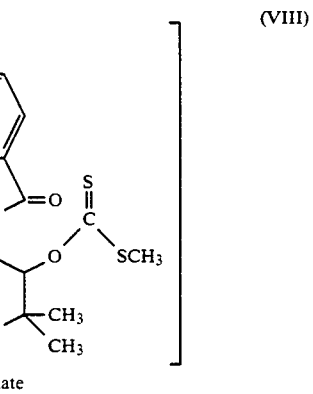 (VIII)

a xanthate wherein $R^1$ and $R^4$ are as defined above.

The intermediate xanthate (VIII), without isolation, is heated and directly converted to the desired product of formula (IX)

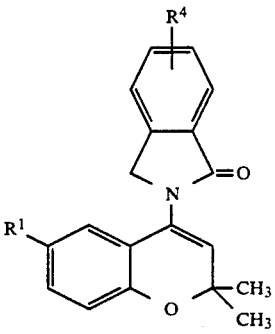 (IX)

wherein $R^1$ and $R^4$ are as defined above.

It is particularly preferred that the reaction between the compounds of formula (IV) and (V) is carried out under alkylation conditions so as to facilitate the formation of the desired bonds, for example, by heating in the presence of potassium carbonate.

The present invention also provides a process for the reaction of the compound (VIIb) with methanesulfonyl chloride in the presence of triethylamine to form the methanesulfonate of formula (X)

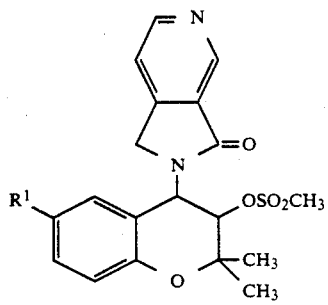

wherein R¹ is as defined above.

The intermediate methanesulfonate (X) is sequentially treated with sodium iodide at room temperature followed by 1,8-diazabicyclo[5.4.0]undec-7-ene at 70° to 90° C. to produce the desired product of formula (XI)

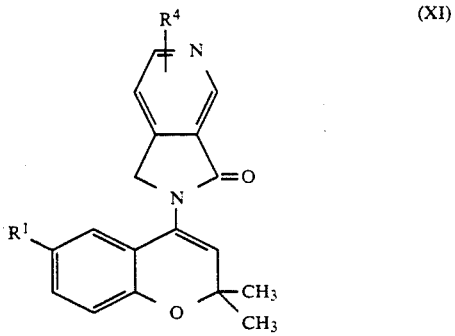

wherein R¹ and R⁴ are as defined above.

Examples of conversions of a group or atom from $R^1{}_1$ into $R^1$ are generally known in the art of synthetic chemistry. For example, if it is desired to obtain a compound of formula (I) wherein R¹ is a trifluoroethoxy group it is possible to convert a compound of formula (I) wherein R¹ is a hydroxy group or a protected hydroxy group to the desired trifluoroethoxy group by deprotecting the hydroxy group and alkylating the hydroxy group in a conventional manner. Examples of protecting agents and their addition and removal are generally known in the art.

The compounds of this invention are capable of forming acid addition salts with therapeutically acceptable acids. The acid addition salts are prepared by reacting the base form of the appropriate compound of formula (I) with one or more equivalents, preferably with an excess, of the appropriate acid in an organic solvent, for example, diethyl ether or an ethanol diethyl ether mixture.

These salts, when administered to a mammal, possess the same or improved pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. ascorbic, citric, lactic, aspartic or tartaric acid; and acids which are sparingly soluble in body fluids and which impart slow-release properties to their respective salts, e.g. pamoic or tannic acid or carboxymethyl cellulose. The preferred salt is the hydrochloride salt. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The compounds of formulas (IV) and (V) are known compounds or can be prepared by conventional procedures from known compounds.

As mentioned previously, the compounds of formula (I) have been found to have blood-pressure lowering activity. They are therefore useful in the treatment of hypertension. These compounds may also be useful in the treatment of asthma, irritable bladder syndrome, and irritable bowel syndrome.

The present invention accordingly provides a pharmaceutical composition which comprises a compound of this invention and a pharmaceutically acceptable carrier. In particular, the present invention provides an antihypertensive pharmaceutical composition which comprises an antihypertensive effective amount of a compound of this invention and a pharmaceutically acceptable carrier.

The compositions are preferably adapted for oral administration. However, they may be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example in a manner similar to that used for known antihypertensive agents, diuretics and β-blocking agents.

The present invention further provides a compound of the invention for use as an active therapeutic substance. Compounds of formula (I) are of particular use in the treatment of hypertension.

The present invention further provides a method of treating hypertension in mammals including man, which comprises administering to the afflicted mammal an antihypertensive effective amount of a compound or a pharmaceutical composition of the invention.

Synthetic Process A relates to the preparation of a compound of formula (I)

Synthetic Process A
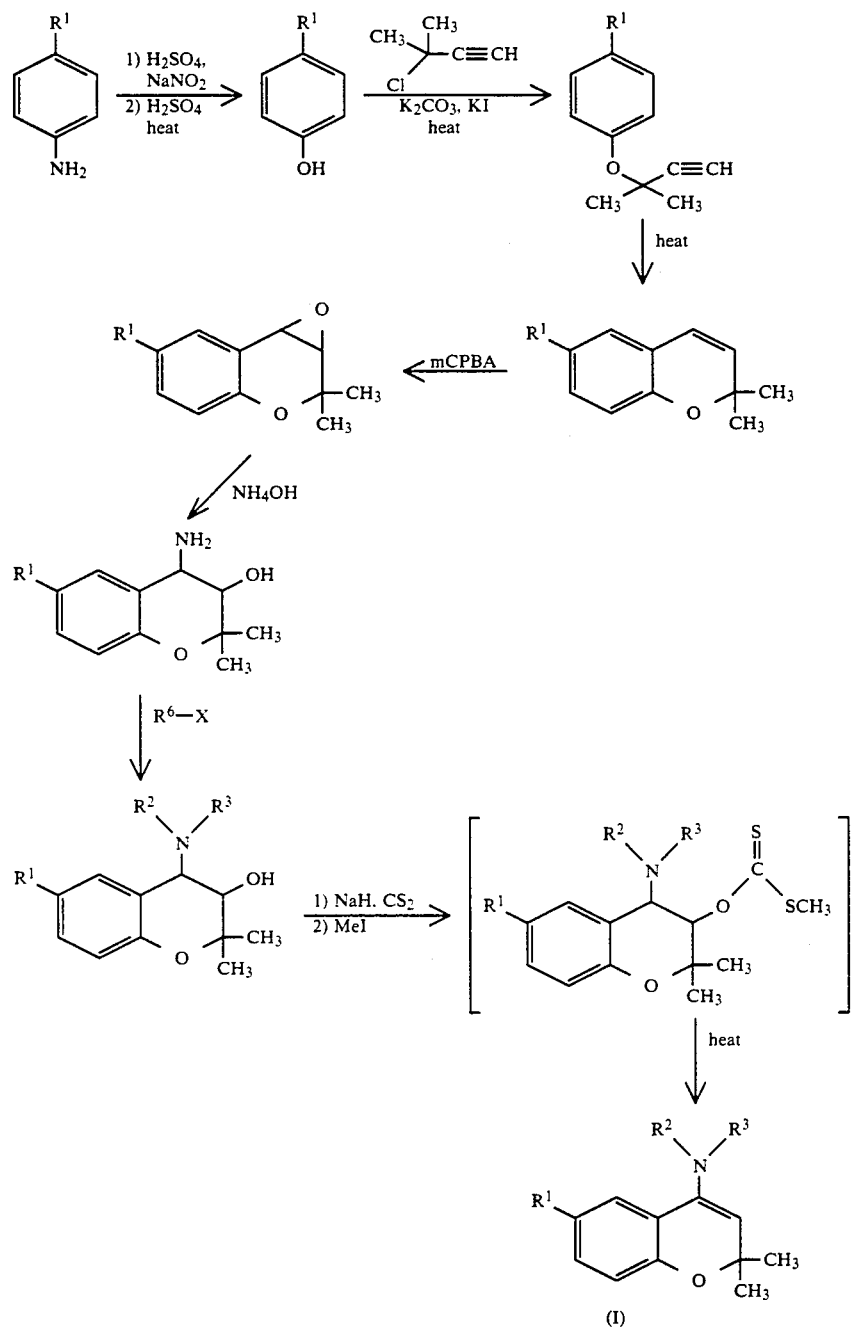
wherein when $R^2$ is hydrogen $R^3$ is benzoyl, furoyl or $R^2$ and $R^3$ are joined to form isoquinolone or isoindolone
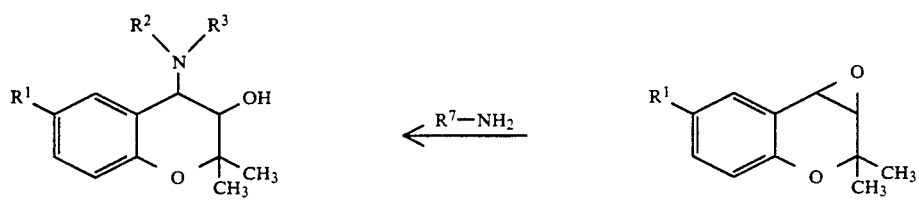

wherein $R^2$ is hydrogen;
$R^3$ is lower alkyl containing 1 to 5 carbon atoms, cyclo lower alkyl containing 5 to 8 carbon atoms or benzyl

↓ $R^8$—X

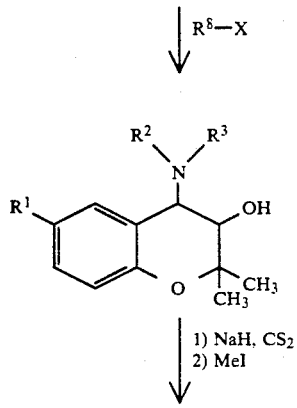

1) NaH, $CS_2$
2) MeI

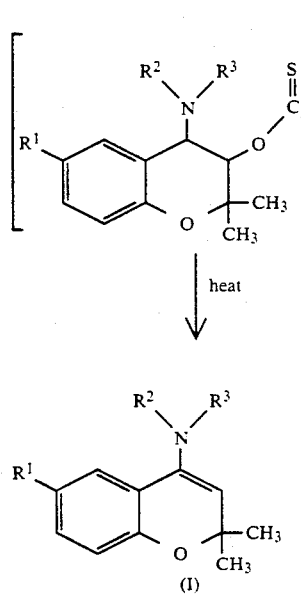

wherein $R^2$ is benzoyl or furoyl and $R^3$ is lower alkyl containing 1 to 5 carbon atoms, cyclo lower alkyl containing 5 to 8 carbon atoms or benzyl -continued $NH_2$—$(CH_2)_m$—$CO_2CH_3$

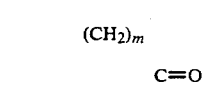

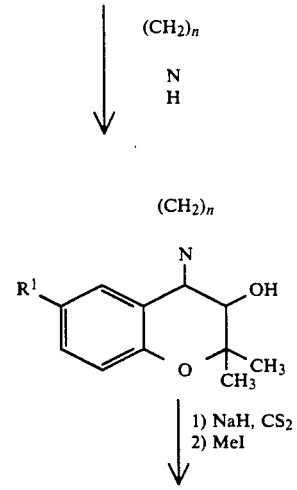

1) NaH, $CS_2$
2) MeI

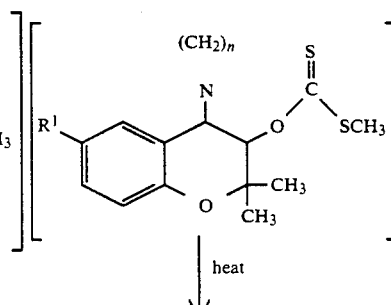

heat

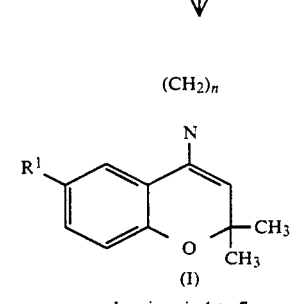

(I)

wherein m is 3 to 6

$(CH_2)_n$

N
H

↓

1) NaH, $CS_2$
2) MeI heat (I)

wherein n is 4 to 7 wherein $R^1$ is defined above; X is chlorine, bromine or iodine; $R^6$ is benzoyl, furoyl, or

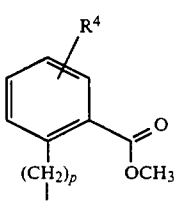

wherein p is 1 or 2; $R^7$ is lower alkyl containing 1 to 5 carbon atoms, cyclo lower alkyl containing 5 to 8 carbon atoms, or benzyl; $R^8$ is benzoyl or furoyl; and $R^4$ is as defined above.

The production of preferred compounds of the present invention is illustrated by Synthetic Process B and Synthetic Process C Synthetic Process B
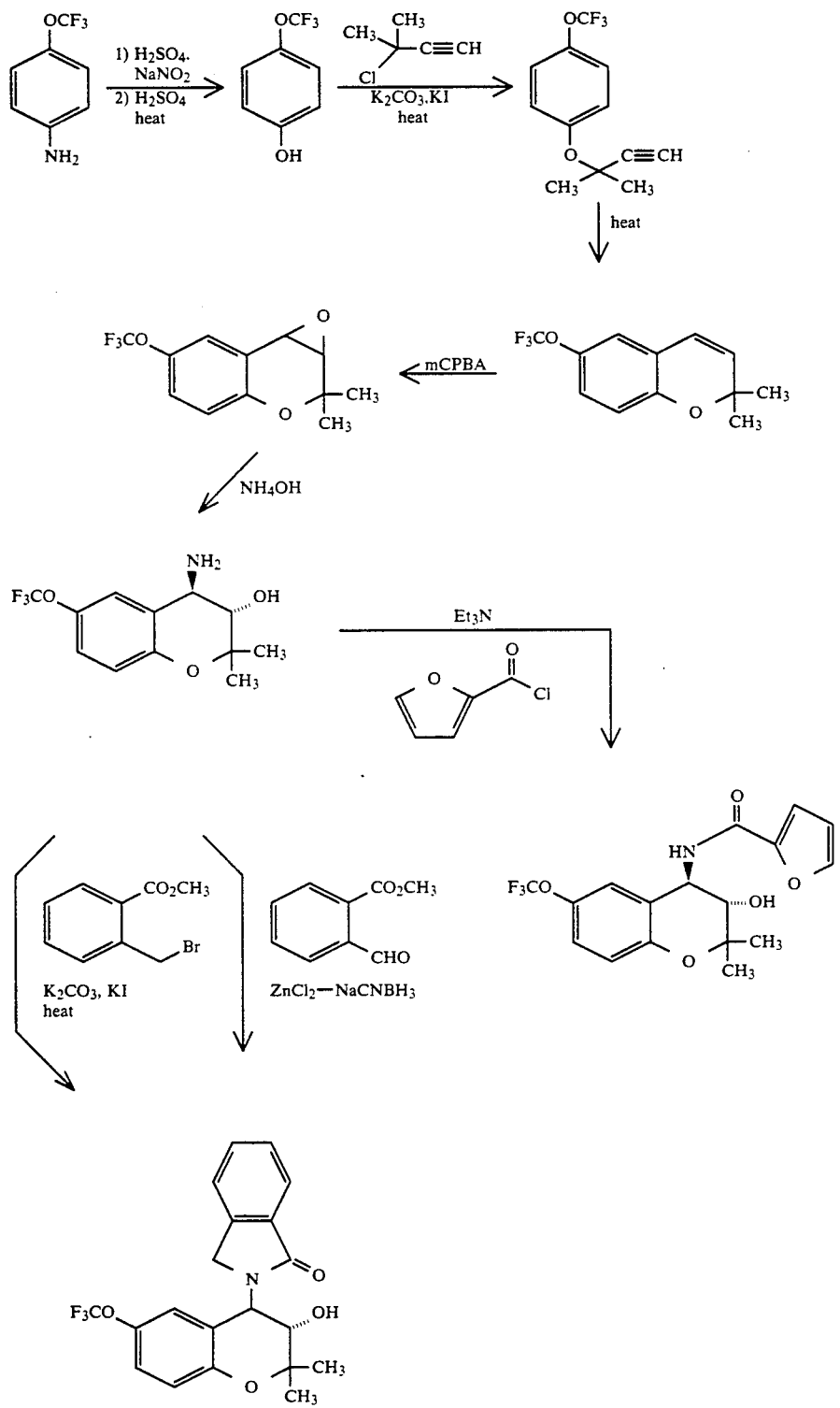

5,171,857
-continued
Synthetic Process B
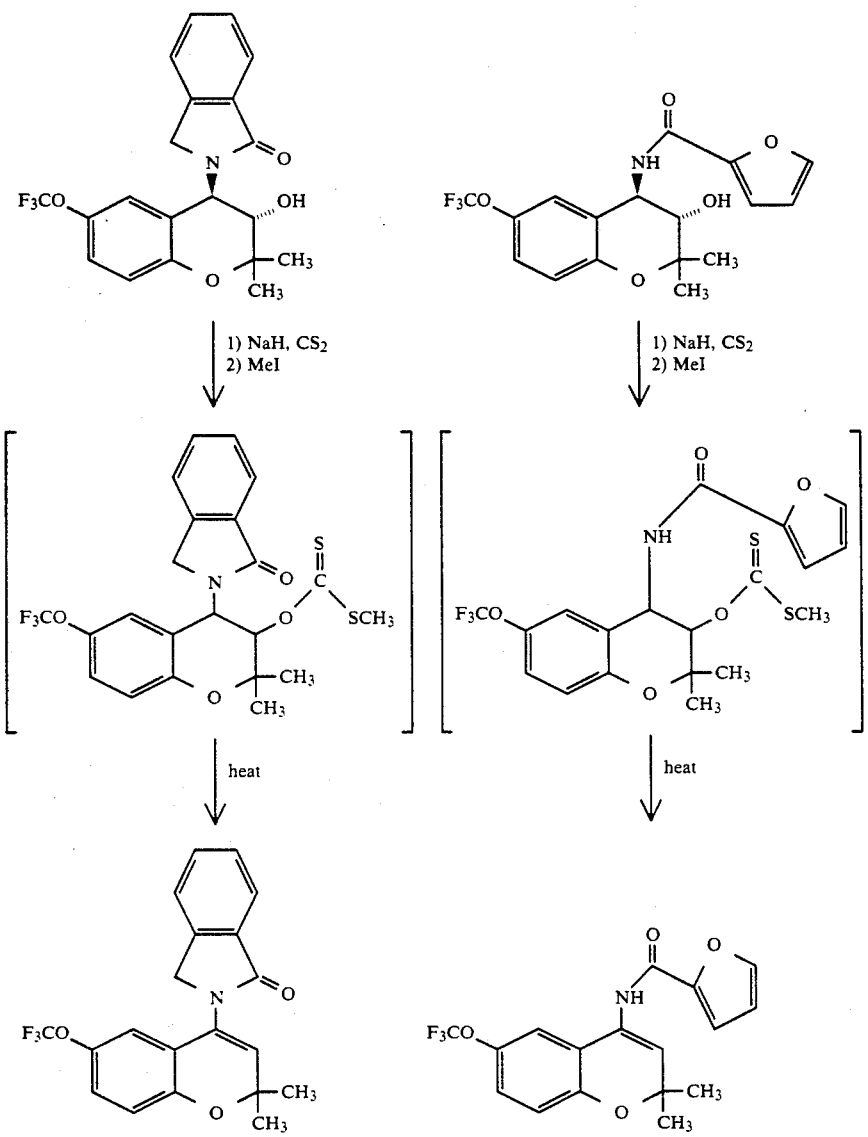
Synthetic Process C
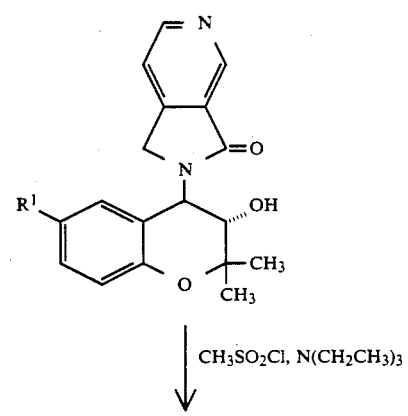
-continued
Synthetic Process C
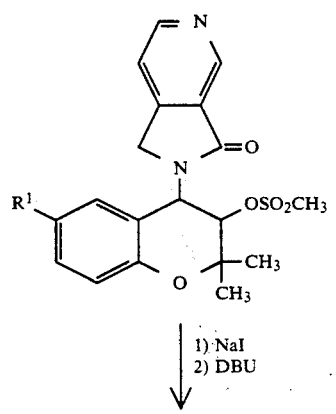

-continued
Synthetic Process C

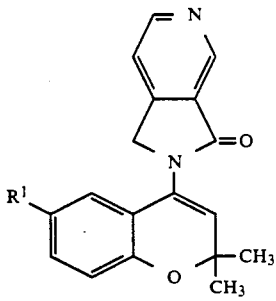

The following examples further illustrate this invention:

EXAMPLE 1

Preparation of p-Trifluoromethoxy Phenol p-Trifluoromethoxy aniline (49.60 g) was added rapidly dropwise to vigorously stirred 9N aqueous H$_2$SO$_4$ (500 mL) at 40° C. The mixture was heated to dissolve the solid, then cooled to 0° C. To the fine white suspension, a solution of sodium nitrite (19.46 g in 50 mL of H$_2$O) was added portionwise until an immediate positive KI/starch test result was obtained. This cold solution of diazonium salt was added rapidly dropwise to 9N aqueous H$_2$SO$_4$ (500 mL) at 110° C. Stirring and heating was continued for 2.5 hours. The mixture was cooled to 10° C. and extracted with diethyl ether (3×500 mL). The combined organic layers were dried (MgSO$_4$), filtered and evaporated in vacuo, then flash chromatographed on SiO$_2$ using diethyl ether as eluant to give 35.0 g of the desired phenol as a light brown oil. The oil was distilled (b.p.=75°-80° C. at 20 torr.) to afford a yellow liquid.

NMR (CDCl$_3$): δ5.06 (1H, s), 6.83 (2H, d, J=9.2 Hz), 7.11 (2H, d, J=9.2 Hz)

EXAMPLE 2

Preparation of 1-[(1,1-Dimethyl-2-propynyl)oxy]-4-(trifluoromethoxy)benzene

To a solution of p-trifluoromethoxy phenol (30.69 g), and 2-methyl-2-chloro-3-butyne (53.00 g) in dry acetonitrile (350 mL) was added potassium iodide (14.30 g) followed by potassium carbonate (95.25 g). This reaction mixture was heated at 70°-80° C. for four days then cooled to room temperature and filtered through celite. The precipitate was washed with dichloromethane and the washings were added to the acetonitrile. The organics were evaporated in vacuo and the oil was taken up in 250 mL of dichloromethane. The organics were washed with water (2×100 mL) and dilute aqueous sodium thiosulfate (2×100 mL), dried (MgSO$_4$), filtered and evaporated in vacuo to leave a dark brown-orange oil. Flash column chromatography on SiO$_2$ using hexane/Et$_2$O (5/1) afforded 34.73 g of the pure product.

NMR (CDCl$_3$) δ1.64 (6H, s), 2.60 (1H, s), 7.05-7.30 (4H, m)

EXAMPLE 3

Preparation of 2,2-Dimethyl-6-(trifluoromethoxy)-2H-1-benzopyran

A solution of 1-[(1,1-dimethyl-2-propynyl)oxy]-4-(trifluoromethoxy)benzene (16.25 g) in 60 mL of quinoline was heated to 175° C. for 2 hours. The solution was cooled to room temperature then ether (250 mL) was added. This mixture was stirred for 15 minutes then decanted from any precipitated tars. The ether solution was washed with 1N aqueous hydrochloric acid (3×200 mL) then water (1×200 mL) and dried (K$_2$CO$_3$). The filtered ether solution was evaporated and flash chromatographed on SiO$_2$ using hexane/ethyl acetate (5/1) as eluant to afford 13.92 g (85%) of the desired bicyclic compound.

Alternate Preparation of 2,2-Dimethyl-6-(trifluoromethoxy)-2H-1-benzopyran

A solution of the 1-[(1,1-dimethyl-2-propynyl)oxy]-4-(trifluoromethoxy)benzene (29.05 g) in 100 mL of chlorobenzene (b.p.=132° C.) was heated to reflux for 24 hours. The reaction mixture was cooled and the solvent removed in vacuo. The oily residue was flash chromatographed on SiO$_2$ using hexane/ethyl acetate (5/1) as eluant to afford 19.72 g of the desired bicyclic compound.

NMR (CDCl$_3$) δ1.42 (6H, s), 5.67 (1H, d, J=10 Hz), 6.28 (1H, d, J=10 Hz), 6.78 (1H, d, J=5.5 Hz), 6.83 (1H, d, J=2 Hz), 6.94 (1H, dd, J=5.5 Hz, 2 Hz)

EXAMPLE 4

Preparation of 1a,7b-Dihydro-2,2-dimethyl-6-(trifluoromethoxy)-2H-oxireno[c][1]benzopyran To a solution of 2,2-dimethyl-6-(trifluoromethoxy)-2H-1-benzopyran (14.37 g) in dichloromethane (40 mL) at 0° C. was added a solution of m-chloroperoxybenzoic acid (mCPBA) (14.22 g) in dichloromethane (160 mL) dropwise. After the addition was complete the ice bath was removed and the temperature allowed to warm slowly to 15° C. whilst stirring for 18 hours. The reaction mixture was filtered, and the precipitate was washed with dichloromethane (50 mL). The combined filtrate was washed with 25% aqueous sodium thiosulfate (2×100 mL), and 50% aqueous sodium bicarbonate (2×100 mL), dried (MgSO$_4$), filtered and evaporated in vacuo. The orange oil was flash chromatographed on SiO$_2$ using hexane/ether (4/1) as eluant to afford 13.36 g of the epoxide as a light yellow oil, which solidified upon standing.

NMR (CDCl$_3$) δ1.25 (3H, s), 1.58 (3H, s), 3.49 (1H, d, J=4 Hz), 3.86 (1H, d, J=4 Hz), 6.78 (1H, d, J=8.5 Hz), 7.11 (1H, dd, J=8.5 Hz and 2 Hz), 7.22 (1H, d, J=2 Hz)

EXAMPLE 5

Preparation of trans-2,3-Dihydro-2,2-dimethyl-3-hydroxy-6-(trifluoromethoxy)-2H-1-benzopyran-4-amine To a solution of 1a,7b-dihydro-2,2-dimethyl-6-(trifluoromethoxy)-2H-oxireno[c][1]-benzopyran (6.18 g) in absolute ethanol (30 mL) at 0° C. was added ammonium hydroxide (45 mL). The reaction mixture was capped with a rubber septum and stirred for four days. The reaction mixture was evaporated in vacuo to remove ethanol and water and the oil was taken up in dichloromethane, dried (Na$_2$SO$_4$) filtered and concentrated in vacuo. The residue was flash chromatographed on SiO$_2$ using dichloromethane/methanol (5/1) as eluant to afford the amino-alcohol, m.p. 176°-182° C. (dec.) recrystallized from chloroform.

Two of the above reactions were run simultaneously to obtain 8.95 g of product.

NMR (DMSO-d$_6$) δ1.07 (3H, s), 1.35 (3H, s), 3.20 (1H, d, J=9.2 Hz), 3.52 (1H, d, J=9.2 Hz), 6.76 (1H, d, J=9 Hz), 7.08 (1H, dd, J=9 Hz, 1.5 Hz), 7.51 (1H, d, J=1.5 Hz)

EXAMPLE 6

Preparation of trans-2-[2,3-Dihydro-2,2-dimethyl-3-hydroxy-6-(trifluoromethoxy)-4H-1-benzopyran-4-yl]-2,3-dihydro-1H-isoindol-1-one To a solution of trans-2,3-dihydro-2,2-dimethyl-3-hydroxy-6-(trifluoromethoxy)-2H-1-benzopyran-4-amine (13.86 g) and methyl 2-formylbenzoate (9.03 g) in 200 mL of dry methanol was added 120 mL of a 0.5 molar solution of zinc chloridesodium cyanoborohydride (0.06 moles each) in dry methanol. After one hour the mixture was warmed to 50°-55° C. and held there with stirring for 14 hours.

The cooled reaction mixture was quenched with 120 mL of saturated aqueous sodium bicarbonate and the methanol was removed in vacuo. 120 mL of water was added to the residue which was then extracted with dichloromethane (3×200 mL). The combined extracts were washed with water (2×300 mL), dried over K$_2$CO$_3$, filtered then evaporated to leave an off-white solid.

This solid was dissolved in 500 mL of hot toluene; the mixture was then heated to reflux for 4 to 5 hours. The solution was then cooled and a white precipitate began to form. The mixture was cooled to 0° C. for 0.5 hours during which time a thick mass of white crystals formed. These crystals were collected by vacuum filtration, washed with hexane/toluene (4/1) and dried in vacuo to yield 18.30 g (93%) of analytically pure product as a white flocculent solid, m.p. 212°-213° C.

Alternate Preparation of trans-2-[2,3-Dihydro-2,2-dimethyl-3-hydroxy-6-(trifluoromethoxy)-4H-1-benzopyran-4-yl]-2,3-dihydro-1H-isoindole-1-one To a solution of trans-2,3-dihydro-2,2-dimethyl-3-hydroxy-6-(trifluoromethoxy)-2H-1-benzopyran-4-amine (3.85 g) and methyl 2-bromomethylbenzoate (3.11 g) in dry acetonitrile (80 mL) was added potassium iodide (1.13 g) then potassium carbonate (powdered, 5.63 g). The reaction mixture was stirred under nitrogen at room temperature for 1 hour then heated in a 75°-80° C. oil bath for 24 hours. The cooled mixture was vacuum filtered through celite. The precipitate was washed with ethyl acetate (75 mL), and the filtrates were combined and evaporated. The residue was taken up in ethyl acetate (175 mL), washed with water (2×100 mL) then 25% aqueous sodium thiosulfate (2×100 mL), dried (MgSO$_4$), filtered and evaporated in vacuo. The resultant oil was crystallized from dichloromethane/ethyl acetate (5/1). The crystals were collected, washed with ether, and dried in vacuo to afford the desired compound in 48% yield, m.p. 212°-213° C.

NMR (DMSO-d$_6$) δ1.24 (3H, s), 1.46 (3H, s), 3.91 (1H, br), 4.06 (1H, br d), 4.48 (1H, br d), 5.24 (1H, br s), 5.77 (1H, d, J=5.8 Hz), 6.70 (1H, br s), 6.92 (1H, d, J=8.9 Hz), 7.17 (1H, dd, J=8.9 Hz and 2.6 Hz), 7.50-7.66 (3H, m), 7.78 (1H, d, J=7.5 Hz)

Anal. Calcd.: C, 61.07; H, 4.61; N, 3.56; Found: C, 60.92; H, 4.87; N, 3.35.

EXAMPLE 7

2-[2,2-Dimethyl-6-(trifluoromethoxy)-2H-1-benzopyran-4-yl]-2,3-dihydro-1H-isoindol-1-one To a stirred solution of trans-2-[2,3-dihydro-2,2-dimethyl-3-hydroxy-6-(trifluoro-methoxy)-4H-1-benzopyran-4-yl]-2,3-dihydro-1H-isoindol-1-one (560 mg) in dry THF at room temperature was added sodium hydride (107 mg, 80% in oil). After 10 minutes, a catalytic amount of imidazole was added and the mixture was warmed to 40° C. for 30 minutes. The oil bath was lowered and carbon disulfide (0.30 mL) was added. After 10 minutes the mixture was warmed to 40° C. for 30 minutes. The oil bath was lowered and methyl iodide (0.31 mL) was added. After 10 minutes the mixture was warmed to 40° C. for 45 minutes. The reaction mixture was then cooled and evaporated to a yellow solid. Methylenechloride (25 mL) was added and the solid removed by filtration. The filtrate was evaporated to a yellow oil.

This oil was heated neat to 165°-170° C. for 2 hours. TLC of an aliquot (eluantether/hexane, 4/1) showed no xanthate and one less polar material. The reaction mixture was flash chromatographed on silica gel using ether/hexane (3/1) as eluant to afford, after evaporation, a white foam. The foam was crystallized using warm hexane and collected by vacuum filtration. Yield of product after vacuum drying was 315 mg (59% yield).

NMR (CDCl$_3$, 400 MHz) δ1.54 (6H, s), 4.62 (2H, s), 5.83 (1H, s), 6.76 (1H, d, J=2.6 Hz), 6.85 (1H, d, J=8.8 Hz), 7.01 (1H, dd, J=8.8 Hz and 2.6 Hz), 7.49 (1H, d), 7.53 (1H, t), 7.62 (1H, dt) and 7.93 (1H, d)

IR (KBr): 1695, 1250, 1160 and 735 cm$^{-1}$

MS: m/e 375 (M+)

Anal. Calcd.: C, 64.00; H, 4.30; N, 3.73; Found: C, 63.84; H, 4.23; N, 3.83.

EXAMPLE 8

2-[2,2-Dimethyl-6-(trifluoromethoxy)-2H-1-benzopyran-4-yl]-1,2-dihydro-3H-pyrrolo[3,4-c]pyridin-3-one To a stirred solution of 2-[(3S,4R)-3,4-dihydro-3-hydroxy-2,2-dimethyl-6-(trifluoro-methoxy)-2H-1-benzopyran-4-yl]-1,2-dihydro-3H-pyrrolo[3,4-c]pyridin-3-one (60 mg) in dry tetrahydrofuran (1 mL) was added triethylamine (0.027 mL). The mixture, under a nitrogen atmosphere, was chilled to 0° C., methanesulfonyl chloride (0.015 mL) was added, and stirring was continued for 16 hours. The reaction mixture which was allowed to warm to room temperature was treated with ethyl acetate (12 mL) and washed with water (2×8 mL). The organic extract was dried (MgSO$_4$), evaporated, and flash chromatographed on SiO$_2$ using ether/ethyl acetate (3/2) to afford pure methane sulfonate (55 mg).

To a solution of the methanesulfonate dissolved in dry dimethylformamide (1.5 mL) was added sodium iodide (57 mg) and the resulting mixture was stirred for 12 hours at room temperature and 3 hours at 45°-50° C. The reaction vessel was removed from the heating bath, 1,8-diazabicyclo[5.4.0]undec-7-ene (DBU) (0.045 mL) was added, and heating was resumed for 3 hours at 80°-85° C. The reaction mixture was cooled and treated with ethyl acetate and washed with water (4×10 mL). The organic phase was dried ($K_2CO_3$) and evaporated to a brown oil. The crude product was purified by flash chromatography on silica gel [ether/ethyl acetate (1/1)] to afford the above titled product (25.5 mg) as a clear oil.

NMR ($CDCl_3$) δ 1.56 (6H, s), 4.76 (2H, s), 5.89 (1H, s), 6.72 (1H, d, J=2 Hz), 6.90 (1H, d, J=8 Hz), 7.06 (1H, dd, J=8 Hz, 2 Hz), 7.68 (1H, d, J=5 Hz), 8.90 (1H, d, J=5 Hz), 9.22 (1H, s).

Pharmacological Data

Male Okamoto-Aoki spontaneously hypertensive rats (SHR) ranging in weight from 250–400 g were anesthetized with halothane. Their left femoral arteries and veins were cannulated with polyethylene tubing of the appropriate size (i.d. 0.023″, o.d. 0.038″). Each animal was placed in a Bollman cage, and the tail, along with two cannulas, was extended through a hole in one end of the cage. The tail was taped securely to a firm rubber board to prevent the rat from turning in its cage to dislodge the cannulas. The femoral arterial cannula was connected to a Statham pressure transducer which in turn was attached to a polygraph for recording arterial pressure and pulse rate. The pulse rate was considered to be the heart rate.

After the blood pressure has stabilized (usually 2 hours after cessation of the anesthesia), standard agonists were injected by the i.v. route. The doses administered were: isoproterenol 0.5 μg/kg, adrenaline 2.0 μg/kg, tyramine 200 μg/kg and angiotensin-I 0.25 μg/kg. The agonists were given in random order except that tyramine was never preceded by isoproterenol as the response to tyramine seemed to be blunted after a prior injection of isoproterenol. Enough time was allowed for the blood pressure to return to preinjection levels before the test compound was administered by gastric lavage. The time of drug administration was designated as time zero. Heart rate and blood pressure were recorded at 5, 10, 15, 30, 45 and 60 minutes and hourly thereafter for a period of 4 hours after drug administration. At 1 and 2 hours post-drug the agonists were again injected at the same concentration and in the same order as during the control period.

For each compound the maximum mean fall in blood pressure was compared to pretreatment control values and expressed as a percentage fall in blood pressure.

The compound 2-[2,2-dimethyl-6-(trifluoromethoxy)-2H-1-benzopyran-4-yl]-2,3-dihydro-1H-isoindol-1-one of the present invention lowers the blood pressure in spontaneously hypertensive rats by 44% at 30 minutes after dosing when administered at a dose of 10 milligrams per kilogram.

The compound 2-[2,2-dimethyl-6-(trifluoromethoxy)-2H-1-benzopyran-4-yl]-1,2-dihydro-3H-pyrrolo[3,4-c]pyridin-3-one of the present invention lowers blood pressure in spontaneously hypertensive rats by 51% at 30 minutes after dosing when administered at a dose of 5 milligrams per kilogram.

Compounds of formula (I) may be administered alone or with a diuretic, such as hydrochlorothiazide, or a b-blocker, such as propranolol or cetamolol in a suitable unit dose form.

We claim:

1. The compound designated 2-[2,2-dimethyl-6-(trifluoromethoxy)-2H-1-benzopyran-4-yl]-1,2-dihydro-3H-pyrrolo[3,4-c]pyridin-3-one or the pharmaceutically acceptable salts thereof.

* * * * *